United States Patent
Ding et al.

(10) Patent No.: US 7,253,166 B2
(45) Date of Patent: Aug. 7, 2007

(54) 6-PHENYL-7H-PYRROLO[2,3-D]PYRIMIDINE COMPOUNDS THAT INDUCE NEURONAL DIFFERENTIATION IN EMBRYONIC STEM CELLS

(75) Inventors: Sheng Ding, San Diego, CA (US); Tom Wu, Quebec (CA); Nathanael S. Gray, San Diego, CA (US); Peter Schultz, La Jolla, CA (US)

(73) Assignees: IRM LLC, Hamilton (BM); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/829,804

(22) Filed: Apr. 22, 2004

(65) Prior Publication Data
US 2005/0038049 A1  Feb. 17, 2005

Related U.S. Application Data

(60) Provisional application No. 60/489,178, filed on Jul. 21, 2003, provisional application No. 60/465,018, filed on Apr. 22, 2003.

(51) Int. Cl.
C07D 413/10  (2006.01)
C07D 487/04  (2006.01)
A61K 31/519  (2006.01)
A61K 31/5355 (2006.01)
A61P 25/28   (2006.01)

(52) U.S. Cl. ............................... 514/234.2; 514/265.1; 544/117; 544/280

(58) Field of Classification Search ................ 544/117, 544/280; 514/234.2, 265, 265.1
See application file for complete search history.

(56) References Cited

U.S. PATENT DOCUMENTS 8,635,762   10/2003   Pfizer, Inc.

FOREIGN PATENT DOCUMENTS

| EP | 682027 | 10/1997 |
|---|---|---|
| WO | WO 1997/27199 | 7/1997 |
| WO | WO 2002/032872 | 4/2002 |
| WO | WO 2002032872 A1 * | 4/2005 |

OTHER PUBLICATIONS

Ding, Sheng; Wu, Tom Y. H.; Brinker, Achim; Peters, Eric C.; Hur, Wooyoung; Gray, Nathanael S.; Schultz, Peter G., Proceedings of the National Academy of Sciences of the United States of America, 100(13), 7632-7637 (English) 2003.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Ding, Sheng; Wu, Tom Y. H.; Brinker, Achim; Peters, Eric C.; Hur, Wooyoung; Gray, Nathanael S.; Schulà, Peter G., Proceedings of the National Academy of Sciences of the United States of America, 100413), 7632-7637 (English) 2003.*

* cited by examiner

Primary Examiner—Mark L. Berch
Assistant Examiner—Susanna Moore
(74) Attorney, Agent, or Firm—Scott W. Reid; D. Phil; The Genomics Institute of the Novartis Research Foundation

(57) ABSTRACT

The invention provides a novel class of compounds and compositions of Formula I:

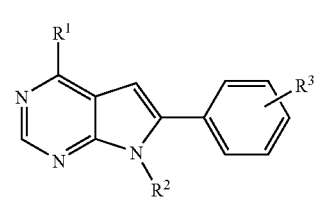

in which $R^1$, $R^2$ and $R^3$ are defined herein, that are useful in the treatment or prevention of diseases or disorders associated with kinases, particularly GSK-3β, c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and c-Met kinases. The invention further relates to the use of the compounds of the invention as potent inducers of neurogenesis in embryonic stem cells.

6 Claims, No Drawings

6-PHENYL-7H-PYRROLO[2,3-D]PYRIMIDINE COMPOUNDS THAT INDUCE NEURONAL DIFFERENTIATION IN EMBRYONIC STEM CELLS

CROSS-REFERENCE TO RELATED APPLICATIONS

This application claims the benefit of priority to U.S. Provisional Patent Application No. 60/465,018 (filed 22 Apr. 2003) and U.S. Provisional Patent Application No. 60/489,178 (filed 21 Jul. 2003). The full disclosures of these applications are incorporated herein by reference in their entirety and for all purposes.

BACKGROUND OF THE INVENTION

1. Field of the Invention

The invention provides a novel class of compounds and compositions that are useful in the treatment or prevention of diseases or disorders associated with kinases, particularly GSK3β, c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and c-Met kinases. The invention further relates to a method of using compounds of the invention to induce neurogenesis in embryonic stem cells.

2. Background

Kinases are involved in many aspects of cellular metabolism, proliferation, differentiation and development. A partial, non-limiting list of kinases include GSK-3β, c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and c-Met. Many diseases are associated with abnormal cellular responses triggered by protein kinase-mediated events. Disease areas include autoimmune diseases, inflammatory diseases, neurological and neurodegenerative diseases, cancer, cardiovascular diseases, allergies and hormone-related diseases. In particular, kinases have been implicated in various diseases including: diabetes; Alzheimer's disease and mood disorders such as bipolar disorder; CNS disorders such as manic-depressive disorder and neurodegenerative diseases; cardiomyocete hypertrophy; and development and regulation of sperm motility. Further, kinases been implicated in hair loss, schizophrenia and neurotrauma, for example, stroke, traumatic brain surgery and spinal cord trauma. These diseases may be caused by, or result in, the abnormal operation of certain cell signaling pathways, for example, those signaling pathways in which GSK3β, c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and c-Met play a role. Accordingly, molecules that modulate the activity of kinase-mediated signaling are useful as therapeutic agents in the treatment of such diseases. Further, the identification of small molecules that permit precise regulation of stem cell renewal and differentiation could facilitate therapeutic applications of stem cells.

SUMMARY OF THE INVENTION

In one aspect, the present invention provides compounds of Formula I:

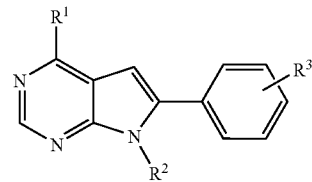

in which:

$R^1$ is chosen from —$OR^4$, —$R^5$ and —$NHR6$; wherein $R^4$ is chosen from $C_{6-10}$aryl and $C_{5-10}$heteroaryl; wherein the aryl or heteroaryl of $R^4$ is optionally substituted by 1 to 3 radicals selected from hydroxy, amino, halo, $C_{1-6}$alkyl, $C_{1-6}$alkoxy, halo-substituted $C_{1-6}$alkyl and halo-substituted-$C_{1-6}$alkoxy; $R^5$ is chosen from $C_{3-8}$heterocycloalkyl optionally substituted by 1 to 3 radicals independently chosen from hydroxy, amino, halo, $C_{1-6}$alkyl, $C_{1-6}$alkoxy, halo-substituted $C_{1-6}$alkyl, halo-substituted-$C_{1-6}$alkoxy and —C(O)$NR^7R^8$; wherein $R^7$ and $R^8$ are independently selected from hydrogen and $C_{1-6}$alkyl; $R^6$ is chosen from $C_{5-10}$heteroaryl and $C_{6-10}$aryl substituted with —$OR^9$; wherein $R^9$ is chosen from $C_{6-10}$aryl and $C_{5-10}$heteraryl;

$R^2$ is selected from the group consisting of hydrogen and $C_{1-6}$alkyl; and $R^3$ is selected from the group consisting of hydrogen, hydroxy, amino, nitro, halo, $C_{1-6}$alkyl, $C_{1-6}$alkoxy, halo-substituted $C_{1-6}$alkyl and halo-substituted-$C_{1-6}$alkoxy; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or an N-oxide derivative, individual isomer or mixture of isomers thereof, or a pharmaceutically acceptable salt thereof, in admixture with one or more suitable excipients.

In a third aspect, the present invention provides a method for treating a disease in an animal in which alteration of the cell signaling pathways in which GSK3β, c-Abl, Bcr-abl, HER-1, HER-2, KDR, Flt-3, c-Raf1, PDGFR-β, c-Kit, Flt-4, Flt-1, Tek, c-src, CDK1, PDK1, FGFR-1, FGFR-2, Fer, MAP3K13, EPHA7 and/or c-Met play a role can prevent, inhibit or ameliorate the pathology and/or symptomology of the disease, which method comprises administering to the animal a therapeutically effective amount of a compound of Formula I or a N-oxide derivative, individual isomer or mixture of isomers thereof; or a pharmaceutically acceptable salt thereof.

In a fourth aspect, the present invention provides a method for inducing neurogenesis in stem cells, the method comprising contacting said cells with a compound of Formula I effective to produce a differentiated neural cell.

In a fifth aspect, the present invention provides the use of a compound of Formula I in the manufacture of a medicament for treating a disease in an animal in which alteration of the cell signaling pathways in which GSK-3β, c-Abl, Bcr-abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and/or c-Met play a role contributes to the pathology and/or symptomology of the disease.

In a sixth aspect, the present invention provides method for inducing neurogenesis in stem cells, the method comprising contacting said cells with a compound of Formula II:

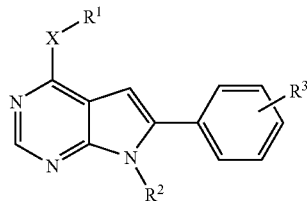

I in which X is selected from the group consisting of a bond, —NR$^4$— and —O—; wherein R$^4$ is hydrogen or C$_{1-6}$alkyl; R$^1$ is selected from the group consisting of C$_{6-10}$aryl, C$_{5-9}$heteroaryl, C$_{3-10}$cycloalkyl and C$_{4-10}$heterocycloalkyl; wherein any aryl, heteroaryl, cycloalkyl or heterocycloalkyl is optionally substituted with 1 to 3 radicals independently selected from the group consisting of hydroxyl, amino, C$_{1-6}$alkoxy, C$_{1-6}$alkyl, —C(O)NR$^5$R$^5$, —C(O)R$^6$, —N(R$^5$)C(O)R$^5$ and —C(O)OR$^5$; wherein R$^5$ is hydrogen or C$_{1-6}$alkyl and R$^6$ is phenyl; R$^2$ is selected from the group consisting of hydrogen and C$_{1-6}$alkyl; and R$^3$ is selected from the group consisting of hydrogen, hydroxyl, amino and nitro; and the pharmaceutically acceptable salts, hydrates, solvates, isomers and prodrugs thereof; effective to produce a differentiated neural cell.

In a seventh aspect, the present invention provides a process for preparing compounds of Formula I and the N-oxide derivatives, prodrug derivatives, protected derivatives, individual isomers and mixtures of isomers thereof; and the pharmaceutically acceptable salts thereof.

In a seventh aspect, the present invention provides methods for screening for compounds that induce neurogenesis and/or gliagenesis.

DESCRIPTION OF THE PREFERRED EMBODIMENTS

The invention provides compounds that are useful in the treatment and/or prevention of diseases or disorders mediated by the cell signaling pathways in which GSK-3β, c-Abl, Bcr-abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and/or c-Met play a role. Also provided are methods for treating such diseases or disorders.

DEFINITIONS

In this specification, unless otherwise defined:

"Alkyl" as a group and as a structural element of other groups, for example halo-substituted-alkyl and alkoxy, can be either straight-chained or branched.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, C$_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, C$_{1-4}$alkyl or a nitrogen protecting group. For example, C$_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Embryonic stem cells" are

"Halogen" (or halo) preferably represents chloro or fluoro, but may also be bromo or iodo.

"Treat", "treating" and "treatment" refer to a method of alleviating or abating a disease and/or its attendant symptoms.

DETAILED DESCRIPTION OF THE INVENTION

The invention provides compounds that are useful for treating or preventing diseases or disorders that are mediated by the cell signaling pathways in which GSK-3 plays a role.

In some embodiments, with reference to compounds of Formula I, R$^1$ is chosen from —OR$^4$, —R$^5$ and —NHR$^6$; wherein R$^4$ is C$_{6-10}$aryl optionally substituted by 1 to 3 radicals selected from hydroxy, amino, halo, C$_{1-6}$alkyl, C$_{1-6}$alkoxy, halo-substituted C$_{1-6}$alkyl and halo-substituted-C$_{1-6}$alkoxy; R$^5$ is chosen from C$_{3-8}$heterocycloalkyl optionally substituted by 1 to 3 radicals independently chosen from hydroxy, amino, halo, C$_{1-6}$alkyl, C$_{1-6}$alkoxy, halo-substituted C$_{1-6}$alkyl, halo-substituted-C$_{1-6}$alkoxy and —C(O)NH$_2$; R$^6$ is chosen from C$_{5-10}$heteroaryl and C$_{6-10}$aryl substituted with —OR$^9$; wherein R$^9$ is C$_{6-10}$aryl;

R$^2$ is selected from the group consisting of hydrogen and C$_{1-6}$alkyl; and

R$^3$ is selected from the group consisting of hydrogen and amino.

In yet a further embodiment, R$^1$ is chosen from phenoxy optionally substituted with 1 to 3 hydroxy radicals, morpholino, piperidinyl optionally substituted with 1 to 3 radicals chosen from hydroxy and —C(O)NH$_2$, phenyl-amino substituted with phenoxy, pyridinyl-amino and 1H-indazol-5-yl.

In a further embodiment, particularly preferred compounds are selected from 3-[6-(3-amino-phenyl)-7H-pyrrolo [2,3-d]pyrimidin-4-yloxy]-phenol, 3-(4-morpholin-4-yl-7H-pyrrolo[2,3-d]pyrimidin-6-yl)-phenylamine, 1-[6-(3-amino-phenyl)-7H-pyrrolo[2,3-d]pyrimidin-4-yl]-piperidine-3-carboxylic acid amide, [6-(3-amino-phenyl)-7H-pyrrolo[2,3-d]pyrimidin-4-yl]-(3-phenoxy-phenyl)-amine, [6-(3-amino-phenyl)-7H-pyrrolo[2,3-d]pyrimidin-4-yl]-pyridin-3-yl-amine, [6-(3-amino-phenyl)-7H-pyrrolo[2,3-d]pyrimidin-4-yl]-(1H-indazol-6-yl)-amine and 1-[6-(3-amino-phenyl)-7H-pyrrolo[2,3-d]pyrimidin-4-yl]-piperidin-3-ol.

In another embodiment the invention provides a method for inducing neurogenesis in stem cells, the method comprising contacting said cells with a compound of Formula II:

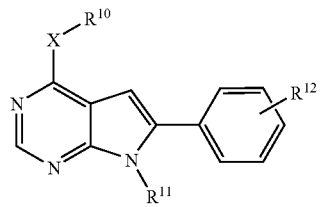

in which X is selected from a bond, —NR$^{13}$— and —O—; wherein R$^{13}$ is hydrogen or C$_{1-6}$alkyl; R$^{10}$ is selected from C$_{6-10}$aryl, C$_{5-9}$heteroaryl, C$_{3-10}$cycloalkyl and C$_{4-10}$heterocycloalkyl; wherein any aryl, heteroaryl, cycloalkyl or heterocycloalkyl is optionally substituted with 1 to 3 radicals independently selected from hydroxyl, amino, C$_{1-6}$alkoxy, C$_{1-6}$alkyl, —C(O)NR$^{14}$R$^{14}$, —C(O)R$^{14}$, —N(R$^{14}$)C(O)R$^{14}$ and —C(O)OR$^{14}$; wherein each R$^{14}$ is selected from hydrogen and C$_{1-6}$alkyl; R$^{14}$ is phenyl; R$^{11}$ is selected from hydrogen and C$_{1-6}$alkyl; and R$^{12}$ is selected from hydrogen, hydroxyl, amino and nitro; and the pharmaceutically acceptable salts, hydrates, solvates, isomers and prodrugs thereof; effective to produce a differentiated neural cell.

In another embodiment, with regard to compounds of Formula II, R$^{13}$ is hydrogen, R$^{10}$ is selected from phenyl, pyridinyl, 1H-indazol-6-yl, morpholino and piperidinyl; wherein phenyl, pyridinyl, 1H-indazol-6-yl, morpholino or piperidinyl is optionally substituted with 1 to 3 radicals independently selected from hydroxyl, amino, methoxy, —C(O)NH$_2$, —C(O)-phenyl, —NHC(O)CH$_3$, —C(O)OH; R$^{11}$ is selected from hydrogen and methyl; and R$^{12}$ is selected from hydrogen and amino.

Preferred compounds of Formula II are detailed in table 1, infra.

In another embodiment, the present invention provides methods for screening for compounds that induce neurogenesis and/or gliagenesis. The methods involve: (a) contacting a polypeptide encoded by a nucleic acid selected from the group consisting of Genbank Accession Number NM_000141(FGFR), Genbank Accession Number NM_003466 (transcription factor, Pax8), Genbank Accession Number NM_005246 (fer (fps/fes related) tyrosine kinase), Genbank Accession Number NM_004721 (MAP3K13 kinase), Genbank Accession Number NM_004440 (EphA7), Celera Accession Number hCT7866, Celera Accession Number hCT14699, Celera Accession Number hCT1648570, Celera Accession Number hCT1641017 (cytokine, CC2), Celera Accession Number hCT11594 (Human 80K-H protein), Celera Accession Number hCT28788 and Celera Accession Number hCT9216 (VPS28 protein) with test compounds to identify one or more modulating compounds that modulate a biological activity of the polypeptide; and (b) testing the modulating compounds for ability to induce neurogenesis and/or gliagenesis.

In another embodiment, the modulating compound reduces the cellular level of the polypeptide. In a further embodiment, the polypeptide is a kinase and the modulating compounds inhibit the kinase activity. Methods for assaying cellular level of a polypeptide or kinase activity are well known in the art, e.g., as described in Sambrook et al., *Molecular Cloning: A Laboratory Manual*, Cold Spring Harbor Press, N.Y., Second (1989) and Third (2000) Editions; and Ausubel et al., *Current Protocols in Molecular Biology*, John Wiley & Sons, Inc., New York (1987-1999).

The effect of the modulating compound on neurogenesis and/or gliagenesis can be tested with a variety of assays routinely practiced in the art. For example, the modulatory compounds can be tested for inducing expression of a specific neuronal marker, for example Tα1 tubulin (Wang, et al., *Nature Biotechnology*, 16, 196, 1998; Roy et al., *Nature Medicine* 6, 271, 2000) as described in Example 4, infra. Alternatively, the effect of the modulating compounds on neurogenesis can be detected by observing the morphology of neuronal cells, for example, P19 cells as described in Example 4.

The invention provides forms of the compound that have the hydroxyl or amine group present in a protected form; these function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes.

Compounds of Formula I can exist in free form or in salt form, e.g. addition salts with inorganic or organic acids. Compounds of Formula I and their salts in hydrate or solvate form are also part of the invention.

When the compounds of Formula I have asymmetric centers in the molecule, various optical isomers are obtained. The present invention also encompasses enantiomers, racemates, diastereoisomers and mixtures thereof. Compounds having the R configuration at this central carbon atom are preferred. Moreover, when the compounds of Formula I include geometric isomers, the present invention embraces cis-compounds, trans-compounds and mixtures thereof. Similar considerations apply in relation to starting materials exhibiting asymmetric carbon atoms or unsaturated bonds as mentioned above.

Methods and Pharmaceutical Compositions for Treating Diseases Associated with Kinase Cell Signaling Pathways The compounds of Formula I in free form or in pharmaceutically acceptable salt form, exhibit valuable pharmacological properties, e.g. GSK-3β, c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and/or c-Met signal modulating properties, for example, as indicated by the assays described in Example 4 and are therefore indicated for therapy.

Compounds of Formula I and II induce neuronal differentiation of up to 80% of embryonic stem (ES) cells and embryonal carcinoma (EC) cells. For example, treatment of a monolayers of P19 cells with 1 μM of Example 1 causes 30-40% of the cells to differentiate specifically into neuronal lineages (based on observations of correct neuronal morphology and immunostaining with multiple neuronal specific markers) while the remaining cells immunostained positively for nestin, indicating they are neuronal progenitor cells. Further, differentiation of the P19 cells into glial and muscle cells were not detected under these conditions.

Additionally, compounds of Formula I and II inhibit c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and c-Met by more than 70% at concentrations of 10 μM. For example, c-Abl, HER-1, HER-2, KDR, PDGFR-β, c-Kit, Flt-4, Flt-1, Tek and c-src are 100% inhibited by 10 μM of example 1. The $IC_{50}$s of Example 1 against c-Abl, c-Kit and HER-2 are 4.5, 20 and 30 nM, respectively.

Further, compounds of Formula I and II modulate GSK-3β/β-catenin signaling in P19 cells resulting in an increased level of β-catenin, a downstream substrate of GSK-3β in the Wnt signaling pathway (Ding, et al., Synthetic Small Molecules That Control Stem Cell fate, PNAS (2003), 100 (13), 7632-7637. This pathway is implicated in neural induction from pluripotent embryonic stem cells. For example, treatment of P19 cells with 10 μM of Example 1 for 36 hours causes an eleven-fold increase in the activity of β-catenin induced TCF/LEF reporter activity.

The invention, therefore, provides methods for preventing or treating disorders or diseases mediated by cell signaling pathways in which GSK-3β, c-Abl, HER-1, HER-2, KDR, Flt-3, c-Raf1, PDGFR-β, c-Kit, Flt-4, Flt-1, Tek, c-src, CDK1, PDK1, FGFR-1, FGFR-2, Fer, MAP3K13, EPHA7 and/or c-Met play a role. These methods involve administering to a subject in need of such treatment an effective amount of a compound of Formula I or II or pharmaceutically acceptable salt thereof, or administering a therapeutically effective amount of stem cells treated with a compound of Formula I or II. The invention further provides molecules that precisely regulate stem cell renewal and differentiation. This regulation could facilitate therapeutic applications of stem cells.

Such diseases include: (i) neurodegenerative diseases and conditions such as Alzheimer's disease, Parkinson's disease, Huntington's disease, amyotrophic lateral sclerosis, multiple sclerosis, stroke, cerebral ischemia, AIDS-related dementia, neurodegeneration associated with bacterial infection, multiinfarct dementia, traumatic brain injury and spinal cord trauma; (ii) psychotic disorders and conditions such as schizophrenia, schizophreniform disorder, schizoaffective disorder (delusional or depressive type), substance induced psychotic disorder (for example, psychosis induced by alcohol, amphetamine, cannabis, cocaine, hallucinogens, inhalants, opioids or phencyclidine), personality disorder (paranoid or schizoid type); (iii) mood disorders and mood episodes such as a major depressive episode, a manic or mixed mood episode, a hypomanic mood episode, a depressive episode (with atypical, melancholic or catatonic features), a mood episode with postpartum onset, post-stroke depression, major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder (bipolar I or II disorders) and cyclothymic disorder; (iv) male fertility and sperm motility, diabetes mellitus, impaired glucose tolerance, metabolic syndrome or syndrome X, polycystic ovary syndrome, adipogenesis and obesity, myogenesis and frailty (for example age-related decline in physical performance), acute sarcopenia (for example, muscle atrophy and/or cachexia associated with burns, bed rest, limb immobilization, or major thoracic, abdominal, and/or orthopedic surgery), sepsis, spinal cord injury, hair loss, hair thinning or balding, immunodeficiency and cancer.

The required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of Formula I or II can be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form. Pharmaceutical compositions comprising a compound of Formula I in free form or in pharmaceutically acceptable salt form in association with at least one pharmaceutical acceptable carrier or diluent can be manufactured in conventional manner by mixing with a pharmaceutically acceptable carrier or diluent.

The compounds of Formula I or II can be administered in free form or in pharmaceutically acceptable salt form, for example, as indicated above. Such salts can be prepared in a conventional manner and exhibit the same order of activity as the free compounds.

Also provided by the invention are compounds of Formula I or II, in free form or in a pharmaceutically acceptable salt form for use in treatment of conditions such as those described above. Pharmaceutical compositions, that includes a compound of Formula I in free form or pharmaceutically acceptable salt form, in association with a pharmaceutically acceptable diluent or carrier thereof are also provided by the invention.

Also provided by the invention are methods involving co-administration, e.g. concomitantly or in sequence, of a therapeutically effective non-toxic amount of a compound of Formula I or II and at least a second drug substance. For example, the compounds of Formula I or II can be administered as the sole active ingredient or in conjunction with, e.g. as an adjuvant to, other drugs e.g. a COX-II inhibitor, an anti-depressant or anxiolytic compound, a NK-1 receptor antagonist, a $5HT_{1D}$ receptor antagonist, a SSRI, an antipsychotic compound, an acetyl cholinesterase inhibitor, a tissue plasminogen activator, a neutrophil inhibitory factor, a NMDA receptor antagonist or a potassium channel modulator.

Where the compounds of Formula I or II are administered in conjunction with other therapies, dosages of the co-administered compounds will of course vary depending on the type of co-drug employed, on the specific drug employed, on the condition being treated and so forth.

Also provided by the invention are pharmaceutical combinations, e.g. a kit, comprising a) a first agent which is a compound of Formula I or II as disclosed herein, in free form or in pharmaceutically acceptable salt form, and b) at least one co-agent, e.g. a COX-II inhibitor, an anti-depressant or anxiolytic compound, a NK-1 receptor antagonist, a $5HT_{1D}$ receptor antagonist, a SSRI, an antipsychotic compound, an acetyl cholinesterase inhibitor, a tissue plasminogen activator, a neutrophil inhibitory factor, a NMDA receptor antagonist or a potassium channel modulator. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I or II and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Methods for Preparing Compounds of the Invention

The present invention also includes processes for the preparation of compounds of the invention that modulate the cell signaling pathways in which GSK-3β, c-Abl, HER-1, HER-2, KDR, Flt-3, c-Raf-1, PDGFR-β, c-Kit, Flt-4, Flt-1, Tek, c-src, CDK1, PDK1, FGFR-1, FGFR-2, Fer, MAP3K13, EPHA7 and/or c-Met play a role. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, wherein $R^1$ is —$OR^4$, can be prepared by proceeding as in the following Reaction scheme 1:

Reaction Scheme 1

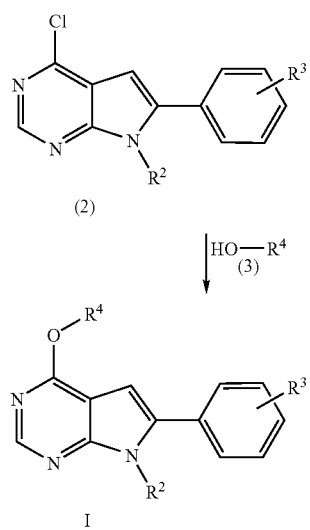

in which $R^2$, $R^3$ and $R^4$ are as defined for Formula I above.

Compounds of Formula I can be prepared by reacting a compound of Formula 2 with a compound of Formula 3. The reaction can be effected in a suitable base (e.g., diisopropylethylamine, or the like), in a suitable solvent (e.g., dioxane, or the like), at a suitable temperature of 130-160° C. and can take 72 hours to complete.

Compounds of Formula I, wherein $R^1$ is —$NHR^6$, can be prepared by proceeding as in the following Reaction scheme 2:

Reaction Scheme 2

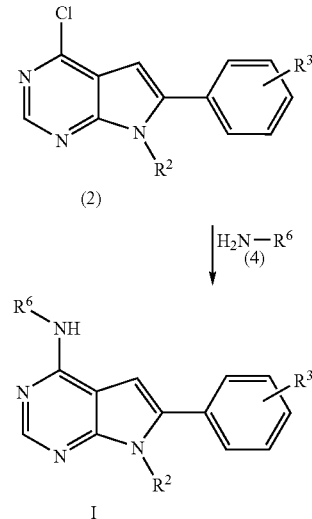

in which $R^2$, $R^3$ and $R^6$ are as defined for Formula I above.

Compounds of Formula I can be prepared by reacting a compound of Formula 2 with a compound of Formula 4. The reaction can be effected in a suitable base (e.g., diisopropylethylamine, or the like), in a suitable solvent (e.g., dioxane, or the like), at a suitable temperature of 110-130° C. and can take up to 12-18 hours to complete.

Compounds of Formula I are prepared according to methods detailed in U.S. Pat. No. 6,140,332.

Additional Processes for Preparing Compounds of the Invention:

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), *Bioorganic and Medicinal Chemistry Letters*, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from the their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) reacting a compound of Formula (2) with a compound of Formula (3) or (4):

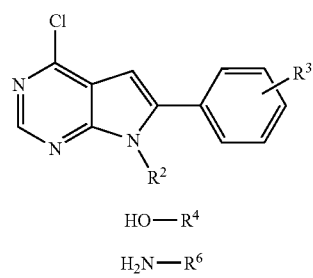

(2)

HO—R$^4$ (3)

H$_2$N—R$^6$ (4)

in which R$^2$, R$^3$, R$^4$ and R$^6$ are as defined for Formula I above; or (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited by, the following examples that illustrate the preparation of compounds of formula I (examples), and their intermediates (References), according to the invention.

Reference 1

6-Bromo-4-chloro-7H-pyrrolo[2,3-d]pyrimidine

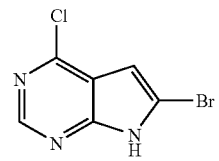

7-Chlorodeazapurine (4.8 g, 31.4 mmol) is suspended in THF (150 mL) and cooled to 0° C. Sodium hydride (1.89 g, 47.1 mmol, 60% dispersion in oil) is added portion wise and stirred at 0° C. for 3 hours. Neat benzene sulfonyl chloride (5.24 mL, 40.8 mmol) is added and the reaction is warmed to room temperature for 6 hours. The reaction is poured into saturated aqueous NH$_4$Cl and extracted with ethyl acetate (EtOAc) three times. The combined organic layer is washed once with brine, dried over anhydrous MgSO$_4$ and concentrated. Flash column chromatography of the crude product using 10% EtOAc in hexane then 100% dichloromethane (DCM) yielded 9.2 g of 7-benzenesulfonyl-4-chloro-7H-pyrrolo[2,3-d]pyrimidine (100%); $^1$H NMR (500 MHz, DMSO) δ 8.81 (s, 1H), 8.12-8.15 (m, 3H), 7.77 (t, J=4.5 Hz, 1H), 7.66-7.67 (m, 2H), 6.96 (d, J=3.7 Hz, 1H); LC-ESMS observed [M+H]$^+$ 294.0 (calculated for C$_{12}$H$_8$ClN$_3$O$_2$S 293.0).

To a solution of 7-benzenesulfonyl-4-chloro-7H-pyrrolo[2,3-d]pyrimidine (9.2 g, 31.4 mmol) in THF (140 mL) at −78° C. is added drop wise 1.5M LDA (23.1 mL, 34.5 mmol) and stirred at −78° C. for 1.5 hours. A solution of BrCl₂CCCl₂Br (20.5 g, 62.8 mol) in THF (45 mL) is added and the reaction is stirred for 2 hours at −78° C. Aqueous saturated NH₄Cl is added slowly and the resulting mixture is warmed to ambient temperature. The aqueous layer is extracted with EtOAc twice. The combined organic layer is washed with brine, dried over anhydrous MgSO₄, and concentrated into a crude solid 7-benzenesulfonyl-6-bromo-4-chloro-7H-pyrrolo[2,3-d]pyrimidine that is carried onto the next step without purification. dissolved in THF (315 mL), solid potassium tert-butoxide (17.6 g, 157 mmol) is added and the reaction mixture is stirred at room temperature overnight. Aqueous saturated NaHCO₃ is added and the aqueous layer is extracted twice with EtOAc. The combined organic layer is washed once with water, brine, dried over MgSO₄, and concentrated. Flash column chromatography of the crude product using 5% acetone in DCM yielded 6.0 g of 6-bromo-4-chloro-7H-pyrrolo[2,3-d]pyrimidine; $^1$H NMR (500 MHz, DMSO) δ 8.57 (s, 1H), 6.79 (s, 1H); LC-ESMS observed [M+H]⁺ 231.9 (calculated for C₆H₃BrClN₃ 230.9).

Reference 2

6-Bromo-4-chloro-7-methyl-7H-pyrrolo[2,3-d]pyrimidine

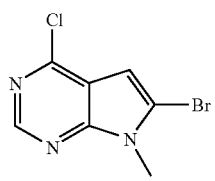

To a solution of 6-bromo-4-chloro-7H-pyrrolo[2,3-d]pyrimidine (122 mg, 0.53 mmol), prepared as in reference 1, in THF (5 mL) at 0° C. is added NaH (31.8 mg, 0.80 mmol, 60% dispersion in oil) portion wise and the reaction mixture is warmed to room temperature for 1 hour. Methyl iodide (103 μL, 1.59 mmol) is added and the mixture is stirred overnight. The reaction is quenched with water and extracted three times with EtOAc. The combined organic layer is washed with brine, dried over MgSO₄, and concentrated. Flash column chromatography of the crude product using 1% MeOH in DCM yielded 100 mg of 6-bromo-4-chloro-7-methyl-7H-pyrrolo[2,3-d]pyrimidine (77%); $^1$H NMR (500 MHz, DMSO) δ 8.64 (s, 1H), 6.96 (s, 1H), 3.79 (s, 3H); LC-ESMS observed [M+H]⁺ 245.9 (calculated for C₇H₅BrClN₃ 244.9).

Example 1

3-[6-(3-Amino-phenyl)-7H-pyrrolo[2,3-d]pyrimidin-4-yloxy]-phenol

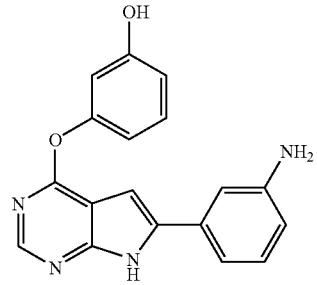

6-Bromo-4-chloro-7H-pyrrolo[2,3-d]pyrimidine (100 mg, 0.41 mmol), prepared as in reference 1, is mixed with resorcinol (451 mg, 4.1 mmol) and diisopropylethylamine (714 μL, 4.1 mmol) in dioxane (1.3 mL). The mixture is heated to 150° C. for 3 days, with stirring. The reaction is then cooled to ambient temperature and the solvent is removed. The resultant crude product is purified by flash column chromatography using a gradient of 3-5% MeOH in DCM to yield 5-(6-bromo-7H-pyrrolo[2,3-d]pyrimidin-4-yloxyl)-phenol (41 mg; 32%).

5-(6-bromo-7H-pyrrolo[2,3-d]pyrimidin-4-yloxyl)-phenol (14 mg, 0.0448 mmol) is mixed with 3-amninophenylboronic acid (13 mg, 0.0896 mmol), Pd(dppf)Cl₂.CH₂.Cl₂ (7.5 mg, 0.009 mmol), and K₃PO₄ (19 mg, 0.0896 mmol) in anhydrous dioxane (0.8 mL) under an argon atmosphere. The mixture is heated to 80° C. for 18 hours, with stirring. The reaction is then cooled to ambient temperature and filtered through a pad of silica with 10% MeOH in DCM. The filtrate is concentrated and the resulting crude product is purified by reverse phase HPLC using a C18 column and 0-95% acetonitrile/water gradient to give 3-[6-(3-aminophenyl)-7H-pyrrolo[2,3-d]pyrimidin-4-yloxy]-phenol (7.1 mg, 50%); $^1$H NMR (500 MHz, DMSO): δ 8.27 (s, 1H), 7.29 (t, J=8.1 Hz, 1H), 7.20 (t, J=7.9 Hz, 1H), 7.10-7.17 (m, 2H), 6.68-7.08 (m, 4H), 6.52 (s, 1H); LC-ESMS observed [M+H]⁺ 319.1 (calculated for C₁₈H₁₄N₄O₂, 318.11).

Example 2

5-[6-(3-Amino-phenyl)-7H-pyrrolo[2,3-d]pyrimidin-4-ylamino]-2-methoxy-phenol

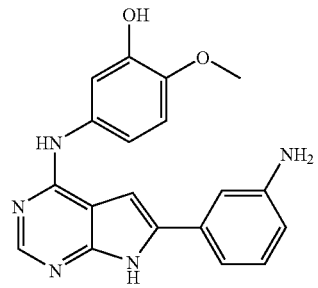

6-Bromo-4-chloro-7H-pyrrolo[2,3-d]pyrimidine (100 mg, 0.41 mmol), prepared as in reference 1, is mixed with 3-hydroxy-4-methoxyaniline (170 mg, 1.22 mmol) and diisopropylethylamine (213 μL, 1.22 mmol) in n-butanol (1.3 mL). The mixture is heated to 120° C. for 18 hours, with stirring. The reaction is then cooled to ambient temperature and the solvent is removed. The resultant crude product is purified by flash column chromatography using a gradient of 3-5% MeOH in DCM to yield 5-(6-bromo-7H-pyrrolo[2,3-d]pyrimidin-4-ylamino)-2-methoxy-phenol (96 mg; 66%); $^1$H NMR (500 MHz, d-methanol) δ 8.17 (s, 1H), 7.16 (s, 1H), 6.98 (d, J=8.6 Hz, 1H), 6.92 (d, J=8.6 Hz, 1H), 6.61 (s, 1H), 3.87 (s, 3H), 3.75 (s, 3H); LC-ESMS observed [M+H]$^+$ 349.0 (calculated for $C_{14}H_{13}BrN_4O_2$, 348.0).

5-[6-(3-amino-phenyl)-7H-pyrrolo[2,3-d]pyrimidin-4-ylamino]-2-methoxy-phenol (15 mg, 0.0448 mmol) is mixed with 3-aminophenylboronic acid (13 mg, 0.0896 mmol), Pd(dppf)Cl$_2$·CH$_2$Cl$_2$ (7.5 mg, 0.009 mmol), and K$_3$PO$_4$ (19 mg, 0.0896 mmol) in anhydrous dioxane (0.8 mL) under an argon atmosphere. The mixture is heated to 80° C. for 18 hours, with stirring. The reaction is then cooled to ambient temperature and filtered through a pad of silica with 10% MeOH in DCM. The filtrate is concentrated and the resulting crude product is purified by reverse phase HPLC using a C18 column and 0-95% acetonitrile/water gradient to give 5-[6-(3-amino-phenyl)-7H-pyrrolo[2,3-d]pyrimidin-4-ylamino]-2-methoxy-phenol (8.6 mg, 55%); $^1$H NMR (500 MHz, DMSO): δ 8.14 (s, 1H), 7.15-7.19 (m, 2H), 7.08-7.09 (m, 2H), 7.02 (d, J=8.3 Hz, 1H), 6.93 (d, J=8.4 Hz, 1H), 6.75 (s, 1H), 6.69 (d, J=8.3 Hz, 1H), 3.88 (s, 3H); LC-ESMS observed [M+H]$^+$ 348.1.

Example 3

5-[6-(3-Amino-phenyl)-7H-pyrrolo[2,3-d]pyrimidin-4-ylamino]-2-methyl-phenol

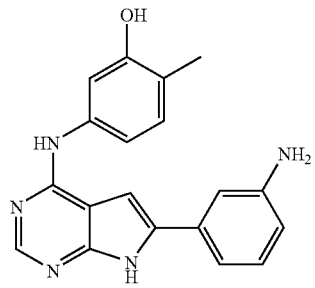

6-Bromo-4-chloro-7H-pyrrolo[2,3-d]pyrimidine (100 mg, 0.41 mmol), prepared as in reference 1, is mixed with 3-hydroxy-4-methylaniline (150 mg, 1.22 mmol) and diisopropylethylamine (213 μL, 1.22 mmol) in n-butanol (1.3 mL). The mixture is heated to 120° C. for 18 hours, with stirring. The reaction is then cooled to ambient temperature and the solvent is removed. The resultant crude product is purified by flash column chromatography using a gradient of 3-5% MeOH in DCM to yield 5-(6-bromo-7H-pyrrolo[2,3-d]pyrimidin-4-ylamino)-2-methyl-phenol (92 mg; 70%).

5-(6-bromo-7H-pyrrolo[2,3-d]pyrimidin-4-ylamino)-2-methyl-phenol (14 mg, 0.0448 mmol) is mixed with 3-aminophenylboronic acid (13 mg, 0.0896 mmol), Pd(dppf)Cl$_2$·CH$_2$Cl$_2$ (7.5 mg, 0.009 mmol), and K$_3$PO$_4$ (19 mg, 0.0896 mmol) in anhydrous dioxane (0.8 mL) under an argon atmosphere. The mixture is heated to 80° C. for 18 hours, with stirring. The reaction is then cooled to ambient temperature and filtered through a pad of silica with 10% MeOH in DCM. The filtrate is concentrated and the resulting crude product is purified by reverse phase HPLC using a C18 column and 0-95% acetonitrile/water gradient to give 5-[6-(3-amino-phenyl)-7H-pyrrolo[2,3-d]primidin-4-ylamino]-2-methyl-phenol (8.6 mg, 59%); $^1$H NMR (500 MHz, DMSO): δ 8.16 (s, 1H), 7.27 (s, 1H), 7.17 (t, J=8.1 Hz, 1H), 7.09-7.10 (m, 2H), 7.04 (d, J=8.1 Hz, 1H), 6.92 (d, J=8.1 Hz, 1H), 6.81 (s, 1H), 6.70 (d, J=7.4 Hz, 1H), 2.19 (s, 3H); LC-ESMS observed [M+H]$^+$ 332.1.

By repeating the procedures described in the above references and examples, using appropriate starting materials, the following compounds of formula I, as identified in Table 1, are obtained:

TABLE I

| Compound Number | Structure | Observed [M + H]$^+$ | $^1$H NMR (500 MHz, d-methanol) |
|---|---|---|---|
| 7 | 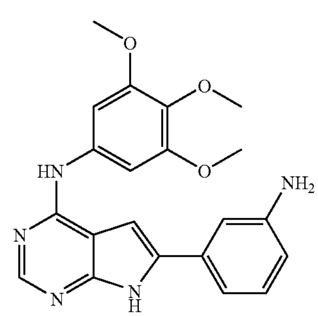 | 392.2 | δ 8.23 (s, 1H), 7.19 (t, J=8.1 Hz, 1H), 7.14 (s, 2H), 7.11–7.12 (m, 2H), 6.90 (s, 1H), 6.71 (d, J=7.7 Hz, 1H), 3.88 (s, 6H), 3.78 (s, 3H). |

TABLE I-continued

| Compound Number | Structure | Observed [M + H]+ | ¹H NMR (500 MHz, d-methanol) |
|---|---|---|---|
| 8 | 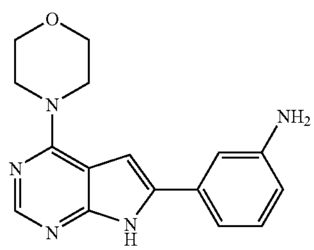 | 296.1 | δ 8.32 (s, 1H), 7.56 (d, J=8.4 Hz, 1H), 7.50 (s, 1H), 7.44 (t, J=8.1 Hz, 1H), 7.29 (s, 1H), 7.09 (d, J=8.1 Hz, 1H), 4.09 (t, J=5.0 Hz, 4H), 3.92 (t, J=5.0 Hz, 4H). |
| 9 | 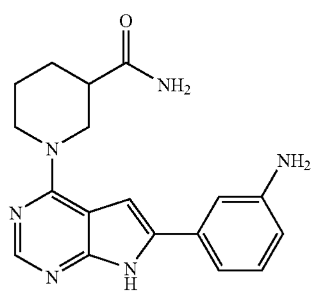 | 337.2 | |
| 10 | 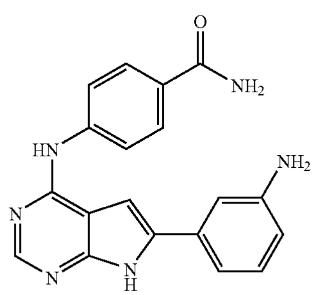 | 345.1 | |
| 11 | 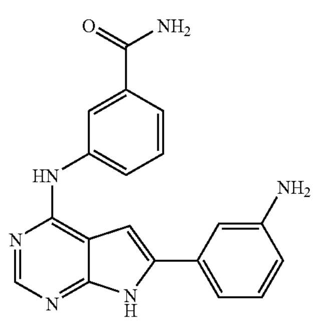 | 345.1 | |
| 12 | 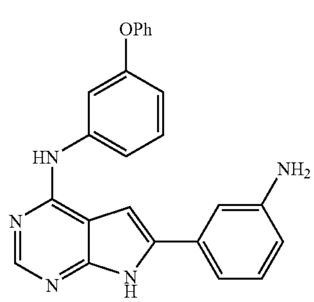 | 394.2 | |

TABLE I-continued

| Compound Number | Structure | Observed [M + H]+ | 1H NMR (500 MHz, d-methanol) |
|---|---|---|---|
| 13 | (pyridin-3-ylamino pyrrolopyrimidine with 3-aminophenyl) | 303.1 | |
| 14 | (1H-indazol-6-ylamino pyrrolopyrimidine with 3-aminophenyl) | 342.1 | |
| 15 | (3-hydroxypiperidin-1-yl pyrrolopyrimidine with 3-aminophenyl) | 310.2 | |
| 16 | (3-hydroxy-4-methoxyphenylamino 6-bromo pyrrolopyrimidine) | 335.0 | |
| 17 | (bis(3-aminophenyl) pyrrolopyrimidine) | 317.1 | δ 8.18 (s, 1H), 7.09–719 (m, 5H), 6.94 (d, J=7.3 Hz, 1H), 6.81 (s, 1H), 6.70 (d, J=8.1 Hz, 1H), 6.53 (d, J=8.1 Hz, 1H). |

TABLE I-continued

| Compound Number | Structure | Observed [M + H]+ | ¹H NMR (500 MHz, d-methanol) |
| --- | --- | --- | --- |
| 18 | (acetamido-phenyl)-NH-pyrrolopyrimidine-(3-aminophenyl) | 359.2 | |
| 19 | (3-carboxyphenyl)-NH-pyrrolopyrimidine-(3-aminophenyl) | 346.1 | |
| 20 | (3-hydroxyphenyl)-NH-pyrrolopyrimidine-(3-aminophenyl) | 318.1 | |
| 21 | (4-hydroxyphenyl)-NH-pyrrolopyrimidine-(3-aminophenyl) | 318.1 | δ 8.11 (s, 1H), 7.37 (d, J=8.6 Hz, 2H), 7.16 (t, J=7.9 Hz, 1H), 7.06–7.07 (m, 2H), 6.82 (d, J=8.6 Hz, 2H), 6.69 (d, J=7.9 Hz, 1H), 6.65 (s, 1H). |
| 22 | (3-hydroxyphenyl)-pyrrolopyrimidine-(3-aminophenyl) | 303.1 | δ 8.73 (s, 1H), 7.55 (d, J=7.7 Hz, 1H), 7.52 (s, 1H), 7.42 (t, J=7.7 Hz, 1H), 7.19–7.24 (m, 3H), 7.08 (s, 1H), 6.98 (d, J=7.5 Hz, 1H), 6.77 (d, J=7.5 Hz, 1H). |

TABLE I-continued

| Compound Number | Structure | Observed [M + H]⁺ | ¹H NMR (500 MHz, d-methanol) |
|---|---|---|---|
| 23 | 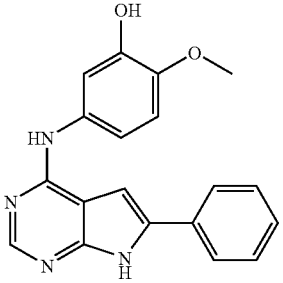 | 333.1 | δ 8.16 (s, 1H), 7.75 (d, J=7.3 Hz, 2H), 7.44 (t, J=7.3 Hz, 2H), 7.32 (t, J=7.3 Hz, 1H), 7.21 (d, J=2.3 Hz, 1H), 7.05 (dd, J=2.3, 8.6 Hz, 1H), 6.93 (d, J=8.6 Hz, 1H), 6.84 (s, 1H), 3.88 (s, 3H). |
| 24 | 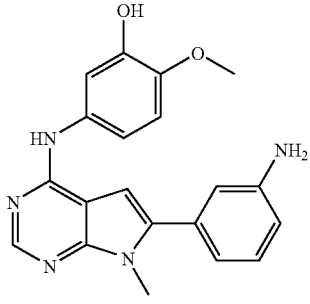 | 362.2 | δ 8.22 (s, 1H), 7.54 (t, J=8.1 Hz, 1H), 7.34–7.39 (m, 2H), 7.26 (d, J=8.1 Hz, 1H), 7.10 (d, J=9.2 Hz, 1H), 6.90–6.95 (m, 3H), 3.93 (s, 3H), 3.89 (s, 3H). |
| 25 | 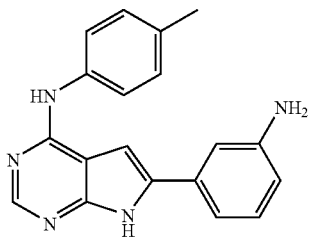 | 316.2 | δ 8.17 (s, 1H), 7.53 (d, J=8.5 Hz, 2H), 7.16–7.21 (m, 3H), 7.09–7.10 (m, 2H), 6.83 (s, 1H), 6.70 (d, J=9.1 Hz, 1H), 2.35 (s, 3H). |

Compounds of Formula I Exhibit Biological Activity as detailed in Example 5.

Example 4

Identification of Molecules that Induce Neuronal Differentiation in P19 Cell Monolayers P19 cells, stably transfected with the pTα1-Luc reporter, are treated with 5 μM (final concentration) of compounds of the invention in MEMα medium with 5% FBS after 12 hours post-plating. Cells are treated for 4 days and lysed to determine luciferase activity by adding luciferase substrate luciferin and measuring the luminescence using a luminometer. Compounds demonstrating activity are confirmed by direct immunostaining with βIII-tubulin/TuJ1 and observation of characteristic neuronal morphology.

Effects of GSK-3β/β-catenin-dependent Signaling upon Treatment of P19 Cells with Compounds of the Invention P19 cells are co-transfected with pTOPFLASH (containing four consensus LEF-1/TCF-1 binding sites, a minimal promoter and a firefly luciferase reporter) and renilla luciferase control reporter (Promega). After 24 hours, the cells are trypsinized and replated into 96-well tissue culture plates and treated with 5 μM (final concentration) of compounds of the invention. Thirty-six hours later, cells are lysed and protein extracts are assayed for luciferase activity. The fold induction offirefly luciferase activity is normalized to renilla luciferase activity. The normalized activities are averaged over three experiments.

It is understood that the examples and embodiments described herein are for illustrative purposes only and that various modifications or changes in light thereof will be suggested to persons skilled in the art and are to be included within the spirit and understanding of this application and scope of the appended claims. All publications, patents, and patent applications cited herein are hereby incorporated by reference for all purposes.

The invention claimed is:

1. A compound of Formula I:

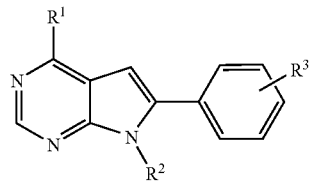

in which:

R¹ is chosen from —OR⁴, —R⁵ and —NHR⁶; wherein R⁴ is chosen from $C_{6-10}$ aryl and $C_{5-10}$ heteroaryl; wherein the aryl or heteroaryl of R⁴ is optionally substituted by 1 to 3 radicals selected from hydroxy, amino, $C_{1-6}$ alkyl and $C_{1-6}$ alkoxy; R⁵ is chosen from $C_{4-8}$ heterocycloalkyl optionally substituted by 1 to 3 radicals independently chosen from hydroxy, amino, $C_{1-6}$ alkyl, $C_{1-6}$ alkoxy and —C(O)NR⁷R⁸; wherein R⁷ and R⁸ are independently selected from hydrogen and $C_{1-6}$ alkyl; R⁶ is chosen from and $C_{6-10}$ aryl R² is selected from the group consisting of hydrogen and $C_{1-6}$ alkyl; and R³ is selected from the group consisting of hydroxy, amino and nitro; and the pharmaceutically acceptable salts thereof.

2. The compound of claim 1 in which:

R¹ is chosen from —OR⁴, —R⁵ and —NHR⁶; wherein R⁴ is $C_{6-10}$ aryl optionally substituted by 1 to 3 radicals selected from hydroxy, amino, $C_{1-6}$ alkyl and $C_{1-6}$ alkoxy R⁵ is chosen from $C_{4-8}$ heterocycloalkyl optionally substituted by 1 to 3 radicals independently chosen from hydroxy, amino, $C_{1-6}$ alkyl, $C_{1-6}$ alkoxy and —C(O)NH₂; R⁶ is chosen from and $C_{6-10}$ aryl;

R² is selected from the group consisting of hydrogen and $C_{1-6}$ alkyl; and

R³ is amino.

3. The compound of claim 2 in which R¹ is chosen from phenoxy optionally substituted with 1 to 3 hydroxy radicals, morpholino, piperidinyl optionally substituted with 1 to 3 radicals chosen from hydroxy and —C(O)NH₂, phenyl-amino pyridinyl-amino and 1H-indazol-5-yl.

4. The compound of claim 1 selected from the group consisting of 3-[6-(3-amino-phenyl)-7H-pyrrolo[2,3-d]pyrimidin-4-yloxy]-phenol, 3-(4-morpholin-4-yl-7H-pyrrolo[2,3-d]pyrimidin-6-yl)-phenylamine, 1-[6-(3-amino-phenyl)-7H-pyrrolo[2,3-d]pyrimidin-4-yl]-piperidine-3-carboxylic acid amide, [6-(3-amino-phenyl)-7H-pyrrolo[2,3-d]pyrimidin-4-yl]-pyridin-3-yl-amine, [6-(3-amino-phenyl)-7H-pyrrolo[2,3-d]pyrimidin-4-yl]-(1H-indazol-6-yl)-amine and 1-[6-(3-amino-phenyl)-7H-pyrrolo[2,3-d]pyrimidin-4-yl]-piperidin-3-ol.

5. A pharmaceutical composition comprising a therapeutically effective amount of a compound of claim 1 in combination with a pharmaceutically acceptable excipient.

6. A method for inducing neurogenesis in P19 stem cells, the method comprising contacting said cells with a compound of claim 1 effective to produce a differentiated neural cell.

* * * * *

UNITED STATES PATENT AND TRADEMARK OFFICE
CERTIFICATE OF CORRECTION

PATENT NO. : 7,253,166 B2 Page 1 of 1
APPLICATION NO. : 10/829804
DATED : August 7, 2007
INVENTOR(S) : Ding et al.

It is certified that error appears in the above-identified patent and that said Letters Patent is hereby corrected as shown below:

Claim 1, Column 25, Line 29 delete "and"

Signed and Sealed this

First Day of April, 2008

JON W. DUDAS
*Director of the United States Patent and Trademark Office*